(12) United States Patent
Krummen et al.

(10) Patent No.: US 8,647,480 B2
(45) Date of Patent: Feb. 11, 2014

(54) APPARATUS FOR PROVIDING A SUBSTANCE FOR THE ANALYSIS OF ISOTOPE RATIOS

(75) Inventors: Michael Krummen, Oldenburg (DE); Hans-Juergen Schlueter, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 110 days.

(21) Appl. No.: 13/178,220

(22) Filed: Jul. 7, 2011

(65) Prior Publication Data

US 2012/0006678 A1 Jan. 12, 2012

Related U.S. Application Data

(62) Division of application No. 11/536,507, filed on Sep. 28, 2006.

(30) Foreign Application Priority Data

Oct. 14, 2005 (DE) .......... 10 2005 049 152

(51) Int. Cl.
*C25B 9/00* (2006.01)

(52) U.S. Cl.
USPC ......... 204/242; 204/275.1; 204/277; 204/278

(58) Field of Classification Search
USPC .................. 204/242, 275.1, 277, 278, 284
See application file for complete search history.

(56) References Cited

U.S. PATENT DOCUMENTS 5,696,378 A * 12/1997 Busch et al. ............. 250/339.12
7,351,316 B2 * 4/2008 Yoshida et al. ............... 204/252

FOREIGN PATENT DOCUMENTS

| DE | 102004010969 A1 | 9/2005 |
| GB | 2388800 A | 11/2003 |
| JP | 2005091180 A | 4/2005 |
| WO | 01/10215 A1 | 2/2001 |
| WO | 200/083988 A2 | 10/2002 |
| WO | 2004/055241 A1 | 7/2004 |

OTHER PUBLICATIONS

Martin et al. Hydrogen and Oxygen Evolution on Boron-Doped Diamond Electrodes, Jun. 1996 The Electrochemical Society, Inc., J. Electrochem. Soc., vol. 143 No. 6, pp. L133-L136.*
Search Report from UKIPO on related patent application No. GB0618321.4 (Dec. 19, 2006).

* cited by examiner

*Primary Examiner* — Arun S Phasge
(74) *Attorney, Agent, or Firm* — Laurence P. Colton; Smith Risley Tempel Santos LLC

(57) ABSTRACT

A method and an apparatus for providing a substance for the analysis of isotope ratios, at least some of the substance being contained in a liquid phase in which the liquid phase is subjected to electrolysis and, in the process, the substance or a pre-product for the latter is formed.

21 Claims, 6 Drawing Sheets

APPARATUS FOR PROVIDING A SUBSTANCE FOR THE ANALYSIS OF ISOTOPE RATIOS

STATEMENT OF RELATED APPLICATIONS

This patent application is a division of U.S. patent application Ser. No. 11/536,507 having a filing date of 28 Sep. 2006, which claims convention priority on German Patent Application No. 10 2005 049 152.9 having a filing date of 14 Oct. 2005, which is incorporated herein by this reference.

BACKGROUND OF THE INVENTION

1. Technical Field

The invention relates to an apparatus for providing a substance for the analysis of isotope ratios, the substance or at least part of the substance being contained in a liquid phase, possibly also in undissolved form. In addition, the invention relates to a device for carrying out an isotope ratio analysis.

2. Prior Art

The analysis of isotope ratios is of interest for an extremely wide range of specialist sectors. For example, the elements C, N, S, O, H, Cl are analyzed, which, for the purpose, should be present in the form of the simplest possible molecules (e.g. $CO_2$), in gaseous form and/or in pure form. Isotope mass spectrometers are preferably used for such analyses. However, other analytical techniques can also be used, for example optical spectroscopy.

The substances to be analyzed are normally not present in the desired form but are constituent parts of larger molecules or compounds, for example complex hydrocarbon compounds or nitrogen compounds. Separating the substances to be analysed out of the complex compounds is in principle possible by means of suitable techniques but always intrinsically involves the risk of isotope fractionation; in addition the preparative effort for routine analysis would be disproportionately high in many cases.

BRIEF SUMMARY OF THE INVENTION

The object of the present invention is to provide a method and apparatus for providing a substance for the analysis of isotope ratios.

The method according to the invention is characterized in that the liquid phase is subjected to electrolysis and, in the process, the substance or a pre-product for the latter is formed. The liquid or mobile phase can itself be the complex compound to be examined or contain the latter in any form, for example as a solution or compound. The liquid phase is subjected to the electrolysis by means of oxidation and/or reduction. In the process, the desired substance to be analysed or a suitable pre-product for this is produced.

The substance or the pre-product for the latter is advantageously formed (during the electrolysis) as a gas (possibly dissolved in the liquid phase) and is incidentally separated from the liquid phase. The substance can be supplied directly to the analytical device provided. In the best case, the substance itself is produced during the electrolysis, for example $N_2$ or $CO_2$, and can be analysed immediately, for example in an isotope mass spectrometer. The pre-product may possibly have to be treated further. The separation of the gas from the liquid phase can be carried out during the electrolysis or following the latter.

Also possible is the formation of a product which is not present as a gas, for example $NO_3$, and which is then reduced by means of suitable additives to a gas, during or after the electrolysis.

The gas formed is preferably carried along by a carrier gas stream, for example helium. The carrier gas can already be supplied during the electrolysis or later and does not have to be dissolved in the liquid phase.

According to a further idea of the invention, the gas formed is incidentally separated physically from the liquid phase, in particular at a membrane. Liquid-impermeable and simultaneously gas-permeable membranes are in principle known.

The electrolysis is preferably carried out on a flowing liquid phase, in particular in a continuous process. This makes the analysis of relatively large quantities or a plurality of different compounds and/or the monitoring of running processes easier. However, the performance of the electrolysis on a stationary liquid phase—in batch operation—is also possible.

According to a further idea of the invention, additives can be supplied to the liquid phase before or during the electrolysis in order to improve or trigger the electrolysis reaction or for the subsequent gas generation. The aim is the most complete conversion possible of the compound of interest during the electrolysis. Here, the additives can also act as a catalyst for the electrolysis reaction or, as a prior reaction, form intermediate products in the electrolysis reaction which convert the substance to be examined.

Likewise possible is the supply of additives, before, during or after the electrolysis, in order to generate gas or intermediate compounds which contain the substance or the pre-product. For example, it is possible that during the electrolysis a substance is formed which remains dissolved in the liquid phase and which gases out only as a result of the addition of an additive. The gas can contain the substance or the pre-product or (as a limiting case) can be the substance or the pre-product itself. An additive preferably reduces the solubility in the liquid phase of the gases formed by the electrolysis. In addition, a salting-out effect can also take place as a result of the additives.

According to a further idea of the invention, there is coupling with a liquid chromatography method. This means that a liquid chromatography method is arranged upstream of the electrolysis, the liquid phase being in particular an eluate from a liquid chromatograph. Since a liquid phase must be present in any case for the electrolysis, coupling with liquid chromatography is particularly advantageous.

According to a further idea of the invention, the substance or the pre-product for this purpose is formed during electrolysis by means of a combination of oxidation and reduction. For example, a more complex nitrogen compound $N_2O$ can be formed by oxidation and $N_2$ can be formed from this by reduction. The nitrogen can then be separated from the liquid phase in a gaseous form. Likewise possible is the formation of $NO_x$ (for example as nitrate) as an oxidation product, which is then reduced to NO or $N_2$ gas.

The apparatus according to the invention for carrying out an isotope ratio analysis is characterized by a device for the performance of electrolysis for the purpose of producing a substance to be analysed or of a pre-product for this purpose from a liquid phase. Devices for isotope analysis are in principle known. What is novel is the integration of an electrolysis device. The latter normally has at least one cavity for the electrolyte and at least two electrodes. Trials have shown that, by means of electrolysis, relatively simple molecules for isotope ratio analysis can be produced from more complex compounds. The electrolysis device can therefore advantageously be used as part of an apparatus for carrying out the isotope ratio analysis.

According to a further idea of the invention, the electrolysis device can have, in addition to the electrodes and the cavity, a feed and a discharge for the liquid phase, a gas outlet and/or a gas inlet. Thus, the construction of a continuously operating device is also possible. Gas produced can be led immediately out of the electrolysis device via the gas outlet, in addition to the reacted liquid phase. Via the gas inlet, for example a carrier gas or a reagent can be supplied.

According to a further idea of the invention, the electrolysis device has a ratio of active surface of an electrode to the volume of the liquid phase in the electrolysis device, specified in square millimeters/cubic millimeters, of >1, in particular >10.

According to a further idea of the invention, the electrolysis device has a channel for the liquid phase, parts of the channel walls simultaneously being surfaces of the electrodes, with a ratio of length to volume, specified in millimeters/cubic millimeters, of >100, in particular >5000 or even >20,000. The aim is the most complete conversion possible of the more complex compound during the electrolysis. Advantageous for this purpose is a minimum residence time in conjunction with close physical proximity to the electrodes.

According to a further idea of the invention, the electrolysis device has one or more channels for the liquid phase, parts of channel walls simultaneously being surfaces of the electrodes, with a meandering course, in particular with more than a hundred changes of direction for each cubic millimeter of channel volume, preferably more than a thousand changes of direction for each cubic millimeter. In this way, axial back-mixing is prevented and turbulence in the liquid phase is increased and, therefore, the conversion reaction is also improved, since more molecules come into the vicinity of the electrodes. As a change of direction, preferably each change in the channel direction by more than 30° is understood, in particular a 90° or even 180° change in the channel course. Preference is given to a course of the channel in one plane with as many 180° changes of direction as possible.

Alternatively, the electrodes can also have a pore structure with many small channels, the latter being flushed through by the liquid phase.

According to a further idea of the invention, the electrolysis device is of plate-like construction with plate-like electrodes, between which a channel plate is held. In this way, one or more channels having a substantially rectangular cross section are formed, the channel plate representing side walls of the channels (given a horizontal orientation of the device) and the electrodes forming upper and lower walls. A channel is preferably machined into the channel plate in the form of a meander, for example in the laser process, by means of water jet cutting or by means of milling.

The electrodes are advantageously held with the central channel plate between two plate-like covers. The covers press the (three) remaining constituent parts firmly together. At least one of the covers is provided with connections and holes for the liquid phase and, if appropriate, for gas.

As an alternative or in addition to the meandering structure, the channels can have built-in fittings for improving the mixing and the flow behaviour, in particular static mixers.

Particularly advantageous is the use of diamond-coated niobium electrodes. These can be obtained, for example, under the trade name DIACHEM. Likewise advantageous are electrodes with or made from gold, stainless steel, Ag, Cu, Zn, Sn, Pt, C (for N measurements).

According to a further idea of the invention, the electrodes have the highest possible overvoltage, in order that little oxygen and hydrogen is formed. A liquid chromatograph is preferably arranged upstream of the electrolysis device and/or a gas exchanger unit is arranged downstream. The overvoltage can be between a few millivolts and several volts, for example for the DIACHEM material about 3 V for oxygen and 2.5 V for hydrogen—the higher the overvoltage the better.

The invention can preferably be applied in the following sectors:
  a) soil analysis, for example analysis of nitrogen components,
  b) foodstuffs analysis, for example analysis of types of sugar,
  c) drug analysis, doping analysis, hormone analysis,
  d) metabolism analysis, for example for amino acids,
  e) geochemistry, for example organic and inorganic acids, acetates,
  f) body of water analysis, for example nitrate analysis,
  g) proof of origin, for example of honey,
  h) biochemical analysis, for example for nucleotides, proteins and plants,
  i) DNA analysis,
  j) genomics/genetic research.

BRIEF DESCRIPTION OF THE DRAWINGS

Further features of the invention incidentally emerge from the claims and the description. Advantageous exemplary embodiments of the invention will be explained in more detail below using drawings, in which:

DETAILED DESCRIPTION OF THE PREFERRED EMBODIMENTS

Figure 1:
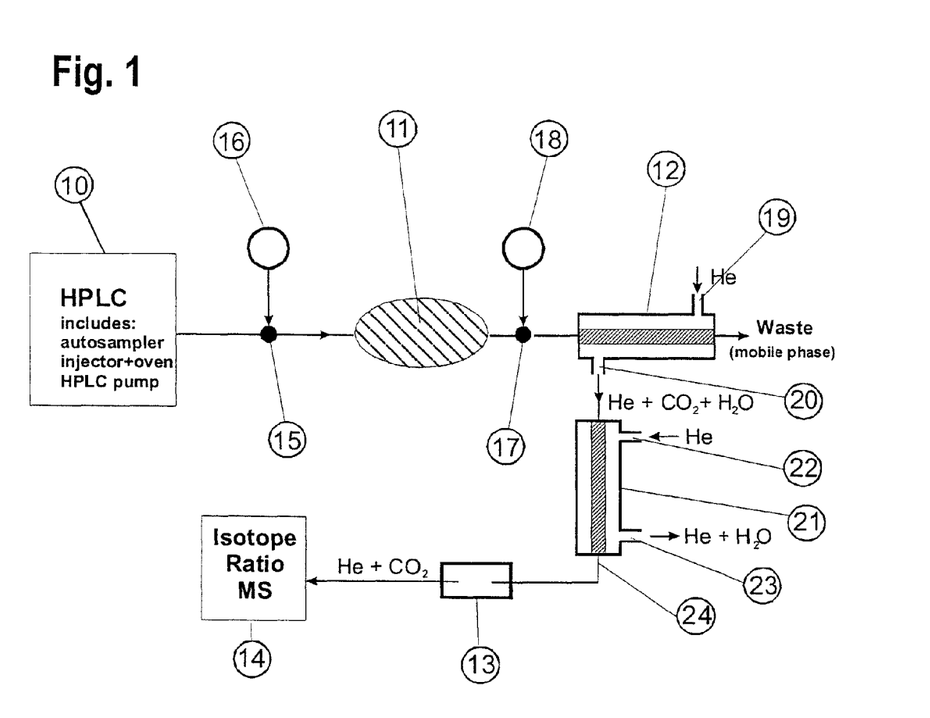
FIG. 1 shows a schematic illustration of an apparatus (overall system) for the isotope analysis of $CO_2$.

An apparatus for carrying out an isotope ratio analysis has, according to FIG. 1, a liquid chromatography device 10, an electrolysis reactor 11, a gas exchanger unit 12, a transfer unit 13 and an isotope mass spectrometer 14.

The liquid chromatograph 10 contains (not shown) conventional components with, for example, autosampler, detector, injector, oven and HPLC pump. Liquid phase coming from the liquid chromatograph (HPLC) 10 and, for example, having an organic carbon compound passes into the electrolysis reactor 11. By means of reaction in the reactor 11, at least $CO_2$ is produced from the liquid phase, is separated from the liquid phase in the gas exchanger unit 12 and, via the transfer unit 13, for example an open coupling, is supplied to the isotope mass spectrometer 14.

Provided between the liquid chromatograph 10 and the electrolysis reactor 11 is a mixing valve 15, via which one or more additives 16 can be introduced into the liquid phase, for example in order to improve the conductivity and/or the electrochemical reaction of the compounds. For instance, acids, inorganic substances, organic substances, salts are used. In a manner analogous to the mixing valve 15, a mixing valve 17 is provided between the reactor 11 and the gas exchanger unit 12, via which valve one or more additives 18 can be supplied to the (electrolytically reacted) liquid phase. These are additives, for example acids or salts, for the degassing of the liquid phase, which may possibly not yet have been carried out or have been carried out inadequately.

In the gas exchanger unit 12, separation is carried out between the liquid phase, on the one hand, and the gas generated by the electrolysis or the additives 18, on the other hand, $CO_2$ in the present case. To this end, the gas exchanger unit 12 is provided with a carrier gas supply 19 and a gas outlet 20. Via the supply 19, helium is supplied, which carries along $CO_2$ and small quantities of water vapour and here supplies it to a water trap 21, in which the water can incidentally be separated from the gas, preferably via a carrier gas supply 22 in conjunction with a gas outlet 23. From a further gas outlet 24, $CO_2$ and carrier gas (helium) reach the transfer unit 13. There, the $CO_2$, as the substance to be analysed, is provided with the helium at the desired dilution for the supply to the isotope mass spectrometer 14.

The gas exchanger unit 12 can also be constructed as a membrane exchanger, gas stripper or the like.

In addition, the gases separated from the liquid phase can be treated still further, for example dried, reduced or oxidized.

In general, the substances produced by reaction in the electrolysis reactor 11 can be designated as fluids. Accordingly, these can be both gases and liquids which are produced from the liquid phase, dissolved in the latter or separated from the latter.

Before entering the electrolysis reactor 11, the liquid phase can comprise both a solvent and a plurality of solvents (mixtures). In addition, the solvents can have inorganic and/or organic buffers.

Figure 2:
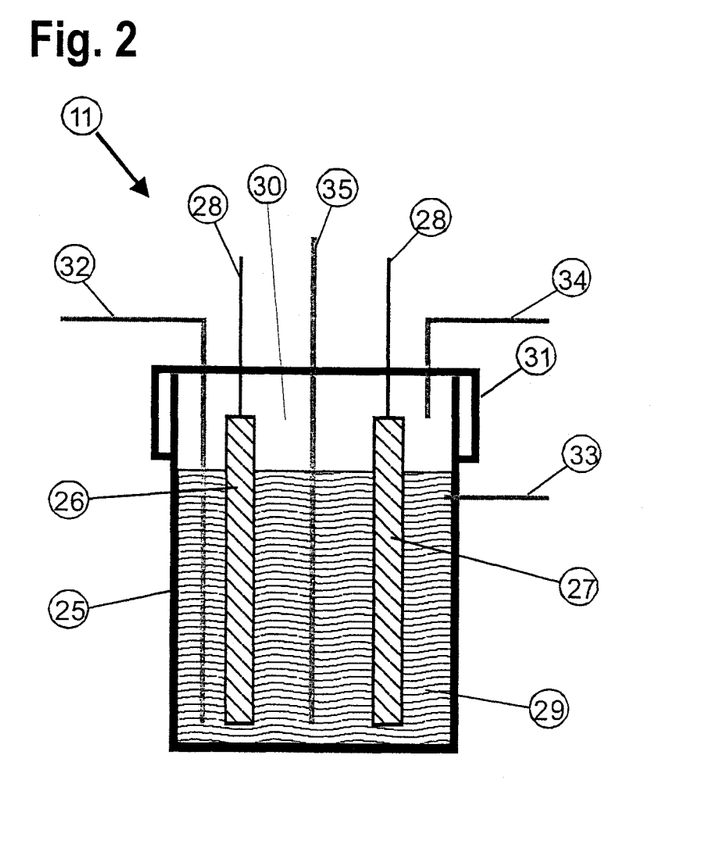
FIG. 2 shows a batch reactor for the electrolysis.

A first example of the electrolysis reactor 11 is shown by FIG. 2. In a pot-like reactor housing 25, two electrodes 26, 27, for example plate-like electrodes, are arranged upright and parallel to each other and are provided with connections 28. The electrodes should have the largest possible surface and can also be formed as grids, with waffle structures, as concentric tubes or in another way with an enlarged surface.

A liquid phase 29 does not fill the housing 25 completely. A gas space 30 remains above the liquid phase 29.

The pot-like housing 25 is covered at the top by a cover 31, which preferably closes tightly. The liquid phase flows into the housing 25 via a feed 32 and leaves the former via a discharge 33.

The gas produced in the reactor 11 passes out of the reactor 11 via a gas outlet 34 at the top in the cover 31. Here, the reactor 11 simultaneously has the function of the gas exchanger unit 12 according to FIG. 1. Via a gas feed 35, carrier gas, for example helium, can be introduced into the reactor 11.

During the electrolysis in the reactor 11, gases are produced which, during or after the electrolysis, are stripped out of the reactor 11 and/or the liquid phase 29 by means of the carrier gas. In addition, a membrane, not shown here, can be provided between the gas space 30 and the liquid phase 29, reducing or even preventing the escape of aerosols into the gas phase.

Figure 3:
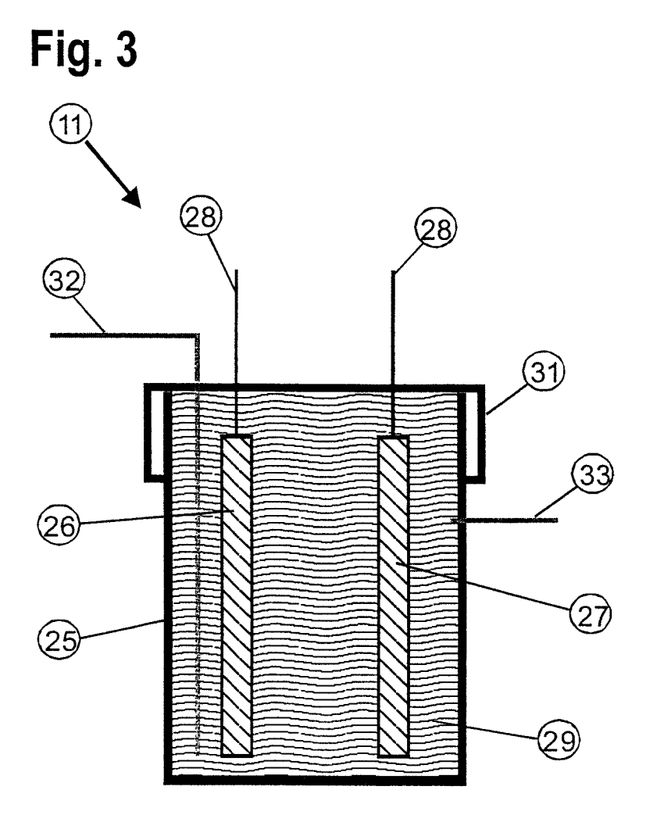
FIG. 3 shows a reactor analogous to FIG. 2 but for a continuously supplied and discharged liquid phase (continuous flow).

While the reactor according to FIG. 2 is provided for the electrolysis in the stationary phase, FIG. 3 relates to the electrolysis with a flowing liquid phase 29, which here fills the housing 25 completely (without any gas space). Via the feed 32, the liquid phase flows into the reactor 11, is reacted there and leaves the reactor 11 via the discharge 33 together with the reaction products, among which the substance to be analysed or a pre-product for the latter will be found.

Extensive modifications of the exemplary embodiments explained by using FIGS. 2 and 3 are possible. For instance, even with a flowing liquid phase (FIG. 3), a gas space corresponding to FIG. 2, a gas feed for carrier gas and/or a gas outlet can be provided, as can a membrane for the improved separation of the gas phase.

Figure 4:
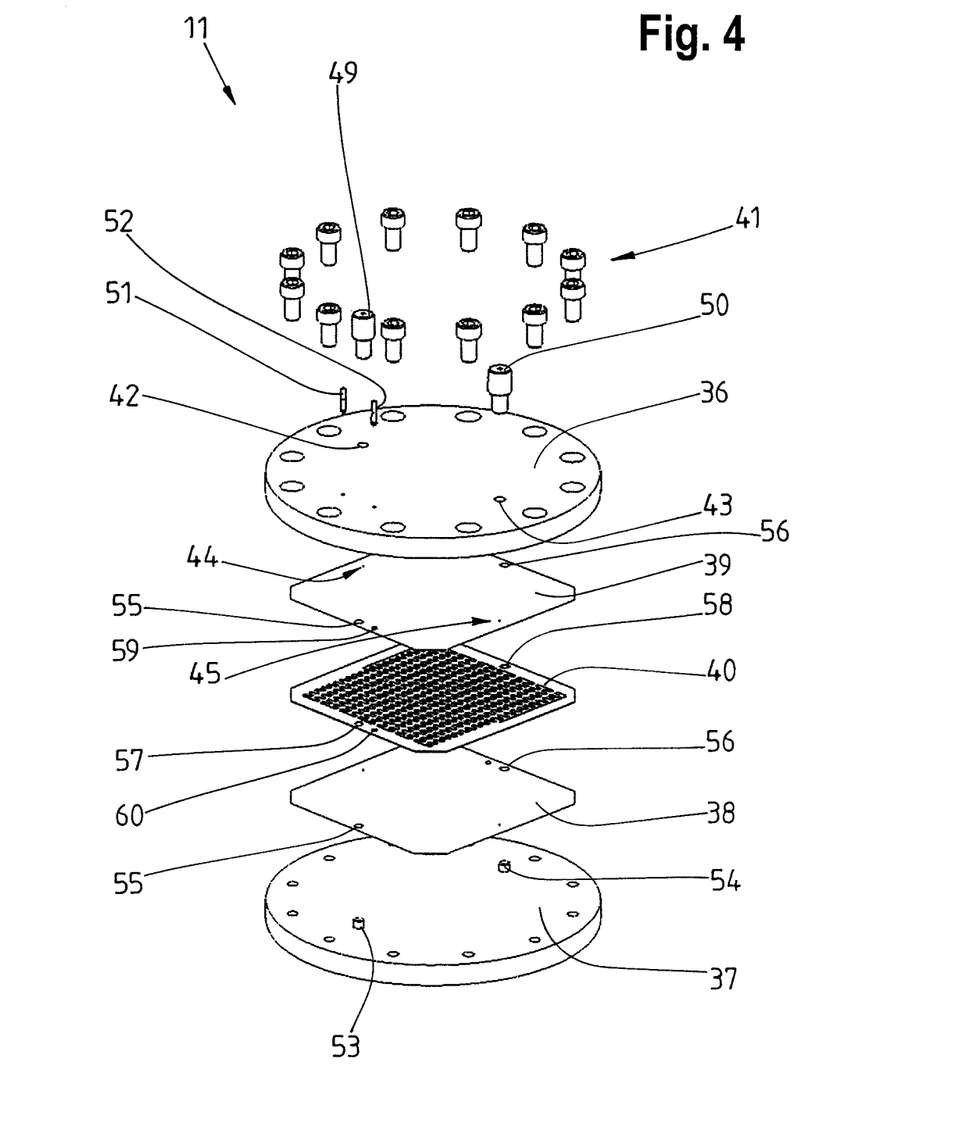
FIG. 4 shows another embodiment of a reactor for the electrolysis with a flowing liquid phase, in an exploded illustration.
Figure 5:
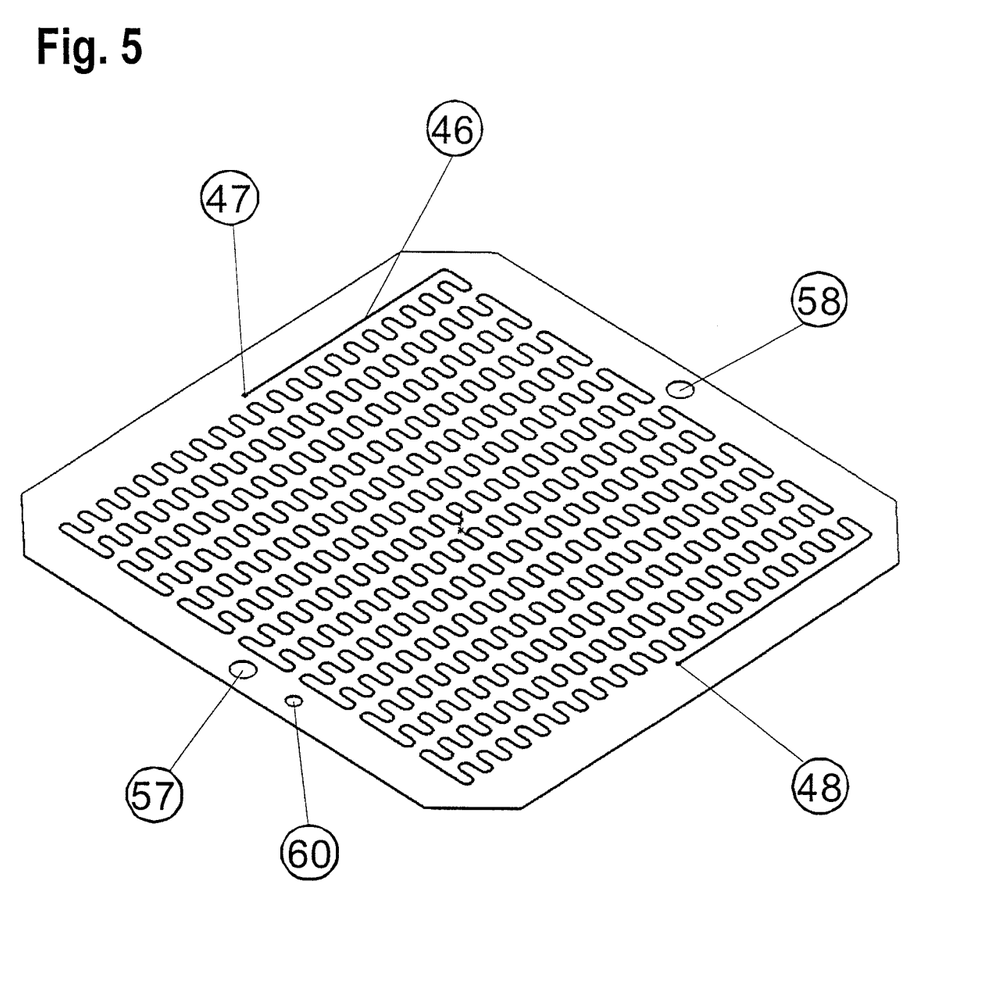
FIG. 5 shows a detail from FIG. 4, specifically a channel plate.

A special embodiment of an electrolysis reactor 11 is shown by FIG. 4. Between an upper cover 36 and a lower cover 37, two plate-like electrodes 38, 39 and, between the latter, a channel plate 40 are held. The two covers 36, 37 are pressed firmly together by means of appropriate screw connections 41; as a result so is the channel plate 40 between the electrodes 38, 39. Electrodes 38, 39 and channel plate 40 are sealed with respect to one another in this way. The liquid phase supplied and led away via holes 42, 43, 44, 45 resides in the reactor 11 exclusively within only one channel 46 in the channel plate 40. The course of the channel 46 can be seen in FIG. 5 and extends from a channel start 47 as far as the channel end 48. The holes 42 to 45 are aligned accurately with the channel start 47 and the channel end 48, respectively. The liquid phase is supplied via a connecting piece 49 inserted into the hole 42 and led away via a connecting piece 50 inserted into the hole 43.

The electric connections provided are contact pins 51, 52, which extend through the upper cover 36 and (only one contact pin 52) through the upper electrode 39 and the channel plate 40. The lower cover 37 is provided with positioning pins 53, 54, which go through the electrodes 38, 39 and the channel plate 40 as far as the upper cover 36 and thus permit accurately fitting positioning of the aforementioned parts in relation to one another. In this case, the positioning pin 53 is arranged closely adjacent to the contact pins 51, 52. For the passage of the positioning pins 53, 54, the electrodes 38, 39 have holes 55, 56, and the channel plate has holes 57, 58. In addition to the holes 55, 57, holes 59, 60 are provided for the passage of the contact pin 52.

Figure 6:
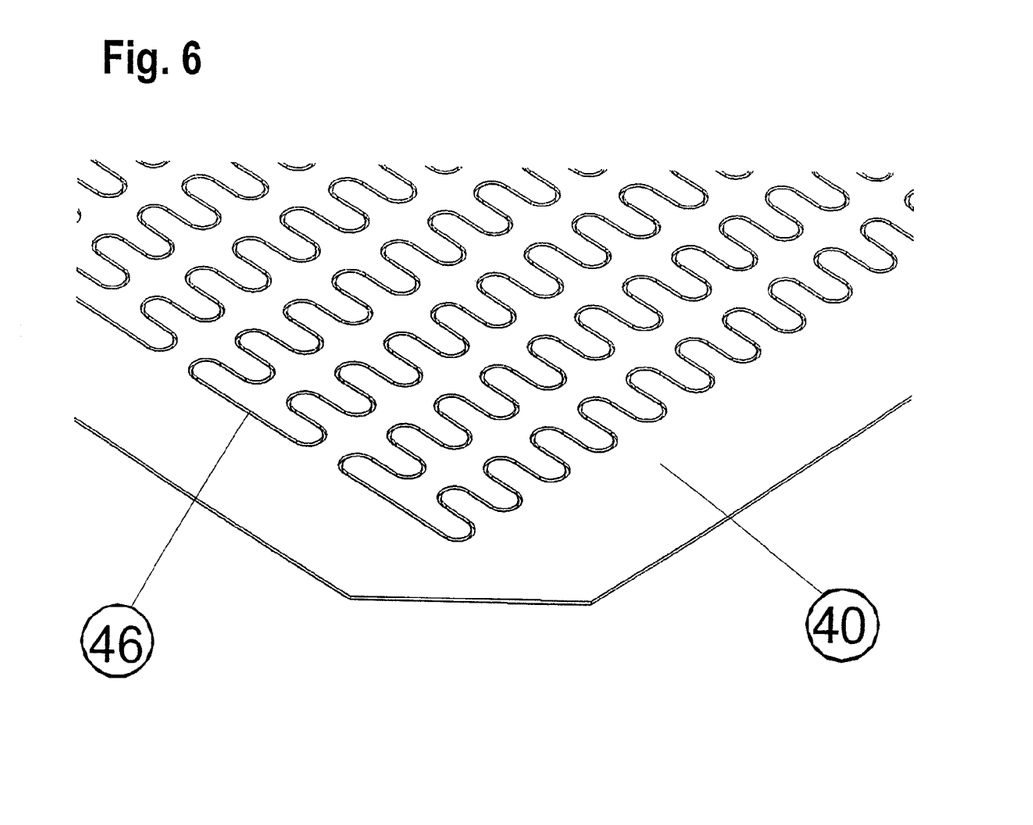
FIG. 6 shows an enlarged illustration of an extract from the channel plate according to FIG. 5.

The channel 46 in the channel plate 40 can be seen in an enlarged illustration in FIG. 6. The channel 46 goes through from the upper side of the channel plate as far as the underside of the same. Given a horizontal arrangement of the channel plate, the material of the channel plate 40 forms the side walls of the channel 46, while the electrodes 38, 39 represent the upper side and underside of the channel cross section closed in this way.

The channel 46 has numerous changes of direction, specifically as many as possible, and is designed in the form of a meander for this purpose. This improves the flow behaviour of the liquid phase and increases the probability that all the particles of the liquid phase come once at some time into the physical proximity of the electrodes required for a reaction. The polarization on the electrodes is preferably changed by an appropriate controller at a cycle rate, for example at a 10-second cycle rate. As a result, OH and H radicals can be produced on both electrodes and can promote oxidation and reduction. In addition, the electrodes are freed from any contaminants as a result.

The electrodes are preferably formed as diamond-coated electrodes, which can be obtained under the trade name DIACHEM.

The channel plate 40 is preferably produced from TEFLON or a material coated with TEFLON. In general, fluorinated or halogenated hydrocarbons, such as CTFE, can be used and other plastics which are suitable for simultaneous sealing and electrical insulation, for example PEEK, CTFE, PTFE, glass, Perspex. Also possible is a composite structure or sandwich structure having a stable layer of stainless steel and external plastic layers or a fibre material (in particular glass fibre) as a matrix with plastic covering or filling.

Modifications of the exemplary embodiments shown are possible. For example, oxidation and reduction can also be carried out not at the same time in one reactor but in different reactors. The mating electrodes used can consist of different materials. For specific oxidations and reductions, the use of one or more reference electrodes is conceivable.

The necessary direct currents and voltages are variable and can be supplied externally or else obtained from the electrochemical voltage from the electrodes themselves.

The incorporation according to the invention of electrolysis into the isotope ratio analysis offers an oxidation potential which is high and can easily be varied. By means of the addition of additives (e.g. sulphates, chlorides), oxidation reactions can be made easier. The novel method is environmentally friendly, since nor or only a few highly reactive chemicals are required. There is the possibility of determining the isotope ratios of nitrogen, sulphur and other substances which can be analysed only with difficulty by known methods. As a consequence, the result is a large number of novel applications, for example in soil research, organic geochemistry, metabolism research, authenticity monitoring, doping monitoring and so on.

LIST OF REFERENCE SYMBOLS

10 Liquid chromatograph (HPLC)
11 Electrolysis reactor
12 Gas exchanger unit
13 Transfer unit
14 Isotope mass spectrometer
15 Mixing valve
16 Additives
17 Mixing valve
18 Additives
19 Carrier gas supply
20 Gas outlet
21 Water trap
22 Carrier gas supply
23 Gas outlet
24 Gas outlet
25 Reactor housing
26 Electrode
27 Electrode
28 Connection
29 Liquid phase
30 Gas space
31 Cover
32 Feed
33 Discharge
34 Gas outlet
35 Gas feed
36 Upper cover
37 Lower cover
38 Electrode
39 Electrode
40 Channel plate
41 Screw connections
42 Hole
43 Hole
44 Hole
45 Hole
46 Channel
47 Channel start
48 Channel end
49 Connecting piece (liquid phase)
50 Connecting piece (liquid phase)
51 Contact pin
52 Contact pin
53 Positioning pin
54 Positioning pin
55 Hole
56 Hole
57 Hole
58 Hole
59 Hole
60 Hole

What is claimed is:

1. An apparatus for carrying out an isotope ratio analysis of C, N, S, O, H, or Cl from organic compounds, comprising:
a device for carrying out electrolysis for the purpose of producing a substance to be analyzed or a pre-product for the substance from a liquid phase (29),
wherein the substance or at least a part of the substance is contained in a liquid phase, the liquid phase is subject to the electrolysis, and, in the process, the substance or the pre-product for the substance is formed, and
wherein the device for carrying out electrolysis comprises a channel (46) for the liquid phase (29), the channel having channel walls parts of which are simultaneously also surfaces of electrodes (38, 39), with a ratio of length to volume of the channel, specified in $mm/mm^3$, of >100.

2. The apparatus as claimed in claim 1, wherein the device for carrying out electrolysis comprises two of the electrodes (26, 27, 38, 39), a cavity, and a feed (32) and a discharge (33) for the liquid phase (29).

3. The apparatus as claimed in claim 1, wherein the device for carrying out electrolysis further comprises a gas outlet (34).

4. The apparatus as claimed in claim 1, wherein the device for carrying out electrolysis further comprises a gas inlet (35).

5. The apparatus as claimed in claim 1, wherein the device for carrying out electrolysis has a ratio of active surface of an electrode (38, 39) to the volume of the liquid phase (29) in the device for carrying out electrolysis, specified in $mm^2/mm^3$, of >1.

6. The apparatus as claimed in claim 1, wherein the channel has a meandering course with more than 100 changes of direction for each $mm^3$ of channel volume.

7. The apparatus as claimed in claim 1, wherein the device for carrying out electrolysis further comprises at least one channel having built-in static mixer fittings to improve the mixing and the flow behaviour.

8. The apparatus as claimed in claim 1, wherein the device for carrying out electrolysis further comprises at least one electrode with a pore structure, many small channels or pores being flushed through by the liquid phase.

9. The apparatus as claimed in claim 1, wherein the electrodes (38, 39) are diamond-coated electrodes.

10. The apparatus as claimed in claim 1, wherein the electrodes (26, 27, 38, 39) have a relatively high overvoltage.

11. The apparatus as claimed in claim 1, further comprising a liquid chromatograph (HPLC 10) arranged upstream of the device for carrying out electrolysis.

12. The apparatus as claimed in claim 1, further comprising a gas exchanger unit (12) arranged downstream of the device for carrying out electrolysis.

13. An apparatus for carrying out an isotope ratio analysis of C, N, S, O, H, or Cl from organic compounds, comprising:
a device for carrying out electrolysis for the purpose of producing a substance to be analyzed or a pre-product for the substance from a liquid phase (29),
wherein the substance or at least a part of the substance is contained in a liquid phase, the liquid phase is subject to the electrolysis, and, in the process, the substance or the pre-product for the substance is formed, and wherein the device for carrying out electrolysis has a ratio of active surface of an electrode (38, 39) to the volume of the liquid phase (29) in the device for carrying out electrolysis, specified in mm$^2$/mm$^3$, of >10.

14. The apparatus as claimed in claim 13, wherein the device for carrying out electrolysis has a ratio of active surface of an electrode (38, 39) to the volume of the liquid phase (29) in the device for carrying out electrolysis, specified in mm$^2$/mm$^3$, of >100.

15. The apparatus as claimed in claim 13, wherein device for carrying out electrolysis comprises a channel (46) for the liquid phase (29), the channel having channel walls parts of which are simultaneously also surfaces of the electrodes (38, 39), with a ratio of length to volume of the channel, specified in mm/mm$^3$, of >5000.

16. The apparatus as claimed in claim 13, wherein the device for carrying out electrolysis comprises a channel (46) for the liquid phase (29), the channel having channel walls parts of which are simultaneously also surfaces of the electrodes (38, 39), with a ratio of length to volume of the channel, specified in mm/mm$^3$, of >20,000.

17. The apparatus as claimed in claim 13, wherein the device for carrying out electrolysis comprises at least one channel (46) for the liquid phase (29), the channel having channel walls parts of which are simultaneously also surfaces of the electrodes (38, 39) and having a meandering course with more than 1000 changes of direction for each mm$^3$ channel volume.

18. The apparatus as claimed in claim 13, wherein the electrodes (38, 39) are diamond-coated niobium electrodes.

19. An apparatus for carrying out an isotope ratio analysis comprising:

a device for carrying out electrolysis for the purpose of producing a substance to be analyzed or a pre-product for the substance from a liquid phase (29), the device for carrying out electrolysis comprising:

a) two electrodes (26, 27, 38, 39), a cavity, and a feed (32) and a discharge (33) for the liquid phase (29);

b) a gas outlet (34) and a gas inlet (35);

c) a ratio of active surface of an electrode (38, 39) to the volume of the liquid phase (29) in the device for carrying out electrolysis, specified in mm$^2$/mm$^3$, of >1;

d) at least one channel (46) for the liquid phase (29), the channel having channel walls parts of which are simultaneously also surfaces of the electrodes (38, 39), with a ratio of length to volume of the channel, specified in mm/mm$^3$, of >100, and with a meandering course with more than 100 changes of direction for each mm$^3$ of channel volume;

e) at least one channel having built-in static mixer fittings to improve the mixing and the flow behaviour; and f) at least one niobium diamond electrode with a pore structure, many small channels or pores being flushed through by the liquid phase, and with a relatively high overvoltage.

20. The apparatus as claimed in claim 19, further comprising a liquid chromatograph (HPLC 10) arranged upstream of the device for carrying out electrolysis.

21. The apparatus as claimed in claim 20, further comprising a gas exchanger unit (12) arranged downstream of the device for carrying out electrolysis.

* * * * *